United States Patent
Hur

(10) Patent No.: US 11,324,718 B2
(45) Date of Patent: May 10, 2022

(54) METHOD FOR PURIFYING CANNABINOIDS

(71) Applicant: NOVASEP EQUIPMENT SOLUTIONS, Pompey (FR)

(72) Inventor: Jin Seok Hur, Glen Mills, PA (US)

(73) Assignee: Sartorius Chromatography Equipment, Pompey (FR)

( * ) Notice: Subject to any disclaimer, the term of this patent is extended or adjusted under 35 U.S.C. 154(b) by 0 days.

(21) Appl. No.: 16/155,646

(22) Filed: Oct. 9, 2018

(65) Prior Publication Data

US 2020/0108044 A1 Apr. 9, 2020

(51) Int. Cl.
*A61K 31/352* (2006.01)
*A61K 36/185* (2006.01)
(Continued)

(52) U.S. Cl.
CPC .......... *A61K 31/352* (2013.01); *A61K 36/185* (2013.01); *B01D 15/1871* (2013.01);
(Continued)

(58) Field of Classification Search
CPC ............ G01N 30/12; G01N 30/02; G01N 2001/4027; G01N 2001/4033; G01N 2030/009; G01N 2030/126; G01N 2030/065; A61K 31/352; A61K 36/185; C07K 1/22; B01D 15/325; B01D 15/185;
(Continued)

(56) References Cited

U.S. PATENT DOCUMENTS

| 5,064,539 A | 11/1991 | Tanimura et al. |
| 5,102,553 A | 4/1992 | Kearney et al. |

(Continued)

FOREIGN PATENT DOCUMENTS

| EP | 0 342 629 A1 | 5/1989 |
| EP | 2040811 B1 | 8/2011 |

(Continued)

OTHER PUBLICATIONS

Sorbent Technologies, "Functionalized Silica Gel, Bonded Phases", Sorbent Technologies, Inc. Internet Archive, https://web.archive.org/web/20160403054148/https://www.sorbtech.com/chromatography/adsorbents/silica-gel/bonded-phases/. Apr. 3. (Year: 2016).*

(Continued)

*Primary Examiner* — Benjamin L Lebron
(74) *Attorney, Agent, or Firm* — Hamilton, Brook, Smith & Reynolds, P.C.

(57) ABSTRACT

The invention relates to a method for the chromatographic purification of at least one cannabinoid compound, wherein the method comprises a main purification stage comprising the steps of: injecting an initial mixture comprising the at least one cannabinoid compound and one or more additional compounds onto a main stationary phase comprising silica particles, the silica particles comprising amino and/or diol groups; performing an elution with an elution solution, and collecting one or more elution fractions; and optionally, washing the main stationary phase with a washing solution and collecting one or more washing fractions; at least one of the elution fractions or washing fractions containing the at least one cannabinoid compound purified from the one or more additional compounds.

20 Claims, 3 Drawing Sheets

(51) Int. Cl.
  *B01D 15/18*   (2006.01)
  *B01D 15/32*   (2006.01)
  *C07K 1/22*   (2006.01)
  *G01N 30/02*   (2006.01)
  *B01D 1/18*   (2006.01)
  *G01N 30/06*   (2006.01)

(52) U.S. Cl.
  CPC .............. *B01D 15/322* (2013.01); *C07K 1/22* (2013.01); *G01N 30/02* (2013.01); *B01D 15/1821* (2013.01); *G01N 2030/065* (2013.01)

(58) Field of Classification Search
  CPC .......... B01D 2215/023; B01D 15/1821; B01D 15/1871; B01D 15/322
  See application file for complete search history.

(56) References Cited

U.S. PATENT DOCUMENTS

| | | | |
|---|---|---|---|
| 5,630,943 A | 5/1997 | Grill | |
| 6,063,284 A | 5/2000 | Grill | |
| 6,136,198 A | 10/2000 | Adam et al. | |
| 6,365,416 B1 | 4/2002 | Elsohly et al. | |
| 6,375,839 B1 | 4/2002 | Adam et al. | |
| 6,403,126 B1 | 6/2002 | Webster et al. | |
| 6,413,419 B1 | 7/2002 | Adam et al. | |
| 6,712,973 B2 | 3/2004 | Adam et al. | |
| 7,479,228 B2 | 1/2009 | Schramm et al. | |
| 7,700,368 B2 | 4/2010 | Flockhart et al. | |
| 8,282,831 B2 | 10/2012 | Kessler et al. | |
| 8,895,078 B2 | 11/2014 | Mueller | |
| 10,239,808 B1* | 3/2019 | Black .................. | B01D 15/322 |
| 2011/0167898 A1* | 7/2011 | Zhou ..................... | G01N 30/24 73/61.55 |
| 2016/0326130 A1* | 11/2016 | Changoer .......... | B01D 11/0288 |
| 2018/0259494 A1* | 9/2018 | Shah .................... | G01N 30/482 |

FOREIGN PATENT DOCUMENTS

| | | | |
|---|---|---|---|
| EP | 1912716 B1 | 4/2015 | |
| GB | 2 393 182 A | 3/2004 | |
| WO | 20050061480 A1 | 7/2005 | |
| WO | 2013/165251 A1 | 11/2013 | |
| WO | 20170108457 A1 | 6/2017 | |
| WO | WO-2017194173 A1 * | 11/2017 | .......... B01D 15/185 |

OTHER PUBLICATIONS

Pacifici, R., et al, "Evaluation of cannabinoids concentration and stability in standardized preparations of cannabis tea and cannabis oil by ultra-high performance liquid chromatography tandem mass spectrometry", Clin Chem Lab Med, 55(10), pp. 1555-1563. (Year: 2017).*
GE Healthcare Bio-Sciences AB, "AxiChrom(TM) Columns". Data file 28-9290-41 AM. Nov. (Year: 2014).*
Dryburgh, L., et al., "Cannabis contaminants: sources, distribution, human toxicitiy and pharmacologic effects", British Journal of Clinical Pharmacology, 84, pp. 2468-2476. (Year: 2018).*
SiliCycle, "Testing and analysis of cannabis products for safety & potency", SiliCycle. Mar. 6. (Year: 2017).*
Lee, "Two Section Simulated Moving Bed Process", Separation Science and Technology 35(4):519-534, 2000.
Zhang, et al., "PowerFeed operation of simulated moving bed units: changing flow-rates during the switching interval", Journal of Chromatography A, 1006 (2003) 87-99.
Henner Schmidt-Traub, "Preparative Chromatography of Fine Chemicals and Pharmaceutical Agents", Wiley-VCH Verlag GmbH & Co. KGaA, 13 pages, 2005, ISBN-13 978-3-527-30643-5.
Wheals et al., "Forensic aspects of high-pressure liquid chromatography", Journal of Chromatography, 122 (1976) pp. 85-105.
Database WPI, Week 201859, Thomson Scientific, London, GB, AN 2018-60553M, XP002796671, & CN 108314608A, Kumming Kandadibiou Commerce & Trade Co Ltd, Jul. 24, 2018 abstract.
Vinson et al., "Studies in laboratory-use reagents III, Simple thin-layer chromatographic system for the separation of cannabinoids", Journal of Chromatography, 106 (1975) pp. 196-199.
Grlic et al., "A simple thin-layer chromatography of cannabinoids by means of silica gel sheets treated with amines", Journal of Chromatography, 48 (1970) pp. 562-564.
International Search Report for International Application No. PCT/EP2019/077106, entitled: Method for Purifying Cannabinoids, dated Apr. 2, 2020.

* cited by examiner

METHOD FOR PURIFYING CANNABINOIDS

TECHNICAL FIELD

The present invention relates to a method for purifying cannabinoids, the method comprising a step of putting an initial mixture containing at least one cannabinoid in contact with a silica-based stationary phase comprising amino and/or diol groups.

TECHNICAL BACKGROUND

For a long time, *Cannabis* has been considered to have medicinal properties for the treatment of various diseases and disorders such as cramps, migraines, convulsions, and attenuation of nausea and vomiting. Therefore, *Cannabis* can be used for example to stimulate the appetite of a person suffering from HIV infection, to treat nausea and vomiting provoked by chemotherapy, or to reduce muscle cramps and spasms in patients suffering from multiple sclerosis.

Cannabinoids are the major active constituents of the plant *Cannabis sativa*. The most important natural cannabinoids present in herbal *Cannabis* are $\Delta^9$-tetrahydrocannabinolic acid ($\Delta^9$-THCA) and cannabidiolic acid (CBDA) with small amounts of the corresponding neutral cannabinoids $\Delta^9$-tetrahydrocannabinol ($\Delta^9$-THC) and cannabidiol (CBD). While $\Delta^9$-THC is psychoactive, CBD is a pharmaceutically active compound devoid of psychoactive activity. Other important cannabinoids are cannabigerol (CBG), cannabinol (CBN), cannabinidiol (CBND) cannabichromene (CBC) and $\Delta^8$-tetrahydrocannabinol ($\Delta^8$-THC).

Although, in some cases, patients may use crude marijuana to reduce or treat their symptoms, this product is less suitable for pharmaceutical applications. It is therefore preferable to separate and purify the cannabinoids present in herbal *Cannabis* in order to use them in pharmaceutical formulations.

In addition, due to the number and amount of phytosanitary substances used for the cultivation of *Cannabis*, it is important to eliminate every trace of phytosanitary substances from the cannabinoid compounds so that they can be used in pharmaceutical formulations.

Similar needs arise in the context of the development of *Cannabis*-derived compositions for recreational use.

Document U.S. Pat. No. 8,895,078 relates to a method for producing an extract from *Cannabis* plant matter, containing tetrahydrocannabinol, cannabidiol and optionally their corresponding carboxylic acids. The document also relates to the production of cannabidiol from the extract.

Documents U.S. Pat. No. 7,700,368 and GB 2 393 182 disclose methods for the preparation of cannabinoids in substantially pure forms starting from plant materials.

Document U.S. Pat. No. 6,403,126 describes a method for extracting cannabinoids, cannflavins and/or essential oils from hemp. The document also describes a method for the production of a hemp extract lacking $\Delta^9$-THC.

Document WO 2013/165251 relates to a method for preparing a $\Delta^9$-THC isolate from a crude solvent extract of *Cannabis* plant material.

Document U.S. Pat. No. 6,365,416 describes a method for preparing THC by extraction of a plant material with a non-polar solvent followed by vacuum distillation and chromatography.

There is still a need for an improved method for purifying cannabinoid compounds, notably allowing separation between cannabinoid compounds and impurities such as phytosanitary substances, as well as allowing separation between the different cannabinoid compounds themselves.

SUMMARY OF THE INVENTION

It is an object of the invention to provide a method for the chromatographic purification of at least one cannabinoid compound, wherein the method comprises a main purification stage comprising the steps of:
- injecting an initial mixture comprising the at least one cannabinoid compound and one or more additional compounds onto a main stationary phase comprising silica particles, the silica particles comprising amino and/or diol groups;
- performing an elution with an elution solution, and collecting one or more elution fractions; and
- optionally, washing the main stationary phase with a washing solution and collecting one or more washing fractions;
at least one of the elution fractions or washing fractions containing the at least one cannabinoid compound purified from the one or more additional compounds.

According to some embodiments, this method further comprises a preliminary purification stage before the main purification stage, said preliminary purification stage comprising the steps of:
- putting a preliminary mixture comprising the at least one cannabinoid compound, the one or more additional compounds and one or more further compounds in contact with a preliminary stationary phase; and
- collecting at least one liquid fraction enriched in the at least one cannabinoid compound and the one or more additional compounds and depleted in the further compounds, said at least one liquid fraction providing the initial mixture.

According to some embodiments, the preliminary stationary phase comprises silica particles comprising amino and/or diol groups.

According to some embodiments, the preliminary purification stage comprises putting the preliminary mixture in contact with the preliminary stationary phase in a suspension solution, to form a suspension; filtering so as to collect a first fraction; optionally, resuspending the preliminary stationary phase in one or more further solutions, and filtering so as to collect one or more further fractions; the liquid fraction enriched in the at least one cannabinoid compound and the one or more additional compounds and depleted in the further compounds being at least one of the first and further fractions.

According to some embodiments, the initial mixture is a *Cannabis* extract.

According to some embodiments, the at least one cannabinoid compound is selected from $\Delta^9$-tetrahydrocannabinol, cannabidiol, cannabinol, cannabigerol, cannabichromene, cannabidivarol, tetrahydrocannabidiol, tetrahydrocannabidivarol, $\Delta^8$-tetrahydrocannabinol, carboxylic acid precursors of the foregoing compounds, related naturally occurring compounds and their derivatives, and combinations thereof.

According to some embodiments, the one or more additional compounds are selected from cannabinoid compounds, pesticides, plant growth regulators and combinations thereof.

According to some embodiments, the one or more further compounds are selected from cannabinoid compounds, pesticides, plant growth regulators and combinations thereof.

According to some embodiments, each of the elution solution and the washing solution is a mixture of a polar solvent and a non-polar solvent; the polar solvent independently being selected from ethanol, methanol and water, and the non-polar solvent being independently selected from pentane, hexane, heptane and octane.

According to some embodiments, each of the elution solution and the washing solution is a mixture of a polar solvent and a non-polar solvent; the elution solution having a volume ratio of non-polar solvent to polar solvent from 99/1 to 50/50; and the washing solution having a volume ratio of non-polar solvent to polar solvent from 1/99 to 50/50.

According to some embodiments, the method further comprises equilibrating the main stationary phase with an equilibration solution in order to equilibrate the main stationary phase for a further injection, the elution solution and the equilibration solution being the same.

According to some embodiments, the method is carried out in an installation chosen from a single column installation, or a multi-column installation having a total bed length smaller than 100 cm.

According to some embodiments, the preliminary purification stage is carried out in an installation chosen from a single column installation, or a multi-column installation having a total bed length smaller than 100 cm, and the main purification stage is carried out in a multi-column installation having a total bed length smaller than 100 cm.

According to some embodiments, the method is carried out in an installation comprising one or more chromatographic columns having a diameter equal to or larger than 5 cm.

According to some embodiments, the installation has a total dead volume lower than or equal to 30% of the total volume of main stationary phase in the installation.

According to some embodiments, the injection of the initial mixture is performed continuously.

According to some embodiments, the injection of the initial mixture is performed in a discontinuous way.

According to some embodiments, the weight proportion of the purified at least one cannabinoid compound relative to the amount of the at least one cannabinoid compound present in the initial mixture is at least 95%.

According to some embodiments, the at least one elution fraction or washing fraction containing the at least one cannabinoid compound purified from the one or more additional compounds further comprises a weight proportion of the one or more additional compounds which is less than 5%, relative to the amount of the one or more additional compounds present in the initial mixture.

According to some embodiments, the preliminary purification stage comprises putting in contact the preliminary mixture with the preliminary stationary phase by injecting the preliminary mixture onto the preliminary stationary phase; performing an elution with an elution solution, and collecting one or more preliminary elution fractions; and optionally washing the preliminary stationary phase with a washing solution and collecting one or more preliminary washing fractions; at least one of said preliminary elution fractions and/or preliminary washing fractions being the liquid fraction enriched in the at least one cannabinoid compound and the one or more additional compounds and depleted in the further compounds.

The present invention makes it possible to address the need mentioned above. In particular the invention provides an improved method for purifying cannabinoid compounds, notably allowing separation between cannabinoid compounds and impurities such as phytosanitary substances as well as allowing separation between the different cannabinoid compounds themselves.

This is achieved by using silica particles which comprise amino and/or diol groups. As a result, the polarity of the silica is increased compared to bare silica, therefore improving separation not only between the cannabinoid compounds and impurities such as phytosanitary substances but also between different cannabinoid compounds present in the same initial mixture.

In some embodiments, the invention makes it possible to purify cannabinoid compounds in a more efficient manner, i.e. with increased yield and/or with increased selectivity and/or within a shorter time and/or with a lower consumption of solvent.

In the prior art of chromatography, some expressions may be used with different meanings. For the sake of clarity, the following definition of the expressions "elution solution" and "washing solution" is presented. Different components of a feed have to be considered, depending on their retention times, compared with the retention time of a non-retained product. These components may be considered as:

weakly retained when their retention times are lower than twice the retention time of a non-retained product; these weakly retained components are collected with the use of an elution solution;
  highly retained when their retention times are from 2 to approximately 15 times the retention time of a non-retained product; these highly retained components are collected with the use of an elution solution and may require a modulation of the eluent strength;
  strongly retained or fixed when their retention times are higher than approximately 15 times the retention time of a non-retained product; these strongly retained components are removed and collected with the use of a washing solution.

An elution solution is thus a solution that can elute weakly and highly retained products. The eluent strength of the elution solution can be increased to decrease the retention times of some components.

A washing solution is a solution with a high elution strength that can remove strongly retained or fixed components from the stationary phase.

DESCRIPTION OF EMBODIMENTS

Figure 1:
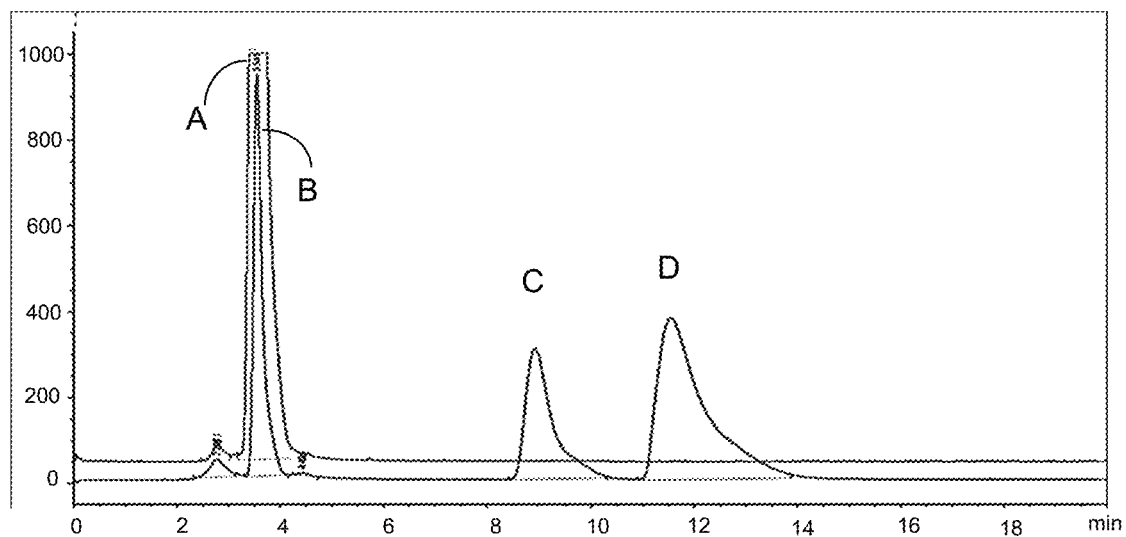
FIGS. 1 to 5 are chromatograms obtained when implementing cannabinoid purification according to various embodiments of the invention, as described in further detail in the example section. The time (in minutes) is shown on the x-axis and the intensity of the signal is shown on the y-axis.

The invention will now be described in more detail without limitation in the following description.

The method of the invention comprises a main purification stage, wherein an initial mixture comprising at least one cannabinoid compound and one or more additional compounds (such as impurities or contaminants) is subjected to chromatographic separation using a main stationary phase comprising silica particles comprising amino and/or diol groups.

Optionally, the method of the invention may also comprise a preliminary purification stage, before the main purification stage, wherein the initial mixture is obtained, starting from a preliminary mixture containing the at least one cannabinoid compound, the one or more additional compounds as well as one or more further compounds.

The starting material of the method of the invention is thus either the initial mixture or the preliminary mixture, depending on whether the preliminary purification stage is present or not.

The at least one cannabinoid compound recovered in a purified form may be used in particular in a therapeutic composition, or in a recreational composition. It can in particular be formulated as an electronic cigarette composition.

Starting Material

Aside from the at least one cannabinoid compound, the one or more additional compounds, and optionally the one or more further compounds, the starting material may notably comprise water or may be a water-based solution. Alternatively, the starting material may comprise or be based on a non-aqueous solvent. Alternatively, the starting material may be in the form of a dry extract.

The starting material may comprise one or more cannabinoid compounds for example derived from a *Cannabis* plant. The term "*Cannabis* plant" refers to wild type *Cannabis sativa* and also variants thereof, including *Cannabis* chemovars which naturally contain different amounts of individual cannabinoids, including also *Cannabis sativa* subspecies *indica* including the variants var. *indica* and var. *kafiristanica*, *Cannabis indica* as well as plants which are the result of genetic crosses, self-crosses or hybrids thereof.

The starting material may comprise at least one cannabinoid compound selected from $\Delta^9$-tetrahydrocannabinol ($\Delta^9$-THC), cannabidiol (CBD), cannabinol (CBN), cannabigerol (CBG), cannabichromene (CBC), cannabidivarol (CBDV), tetrahydrocannabidiol (THCBD), tetrahydrocannabidivarol (THCBDV), tetrahydrocannabigerol (THCBG), tetrahydrocannabichromene (THCBC), $\Delta^8$-tetrahydrocannabinol, carboxylic acid precursors of the foregoing compounds, related naturally occurring compounds and their derivatives.

According to some embodiments the starting material comprises a single cannabinoid compound.

According to some preferred embodiments, the starting material comprises more than one cannabinoid compound. In this case, at least one or possibly several of the cannabinoids are sought to be purified. Others of the cannabinoid compounds may optionally be considered as impurities or contaminants (herein, "additional compounds" and/or "further compounds") and sought to be separated and removed.

Preferably, the starting material comprises at least $\Delta^9$-THC and/or CBD and/or CBN.

According to some embodiments, the starting material may comprise from 5 to 100% of cannabinoid compounds, and preferably from 10 to 100% of cannabinoid compounds, based on the total dry weight of the starting material. The starting material may therefore comprise from 5 to 10%; or from 10 to 20%; or from 20 to 30%; or from 30 to 40%; or from 40 to 50%; or from 50 to 60%; or from 60 to 70%; or from 70 to 80%; or from 80 to 90%; or from 90 to 100% of cannabinoid compounds, based on the total dry weight of the starting material.

When the starting material comprises $\Delta^9$-THC, the $\Delta^9$-THC can represent from 0.01 to 99.9%, and preferably from 0.1 to 95% of the total dry weight of the starting material. For example, $\Delta^9$-THC can represent from 0.01 to 0.1%; or from 0.1 to 0.5%; or from 0.5 to 1%; or from 1 to 2%; or from 2 to 3%; or from 3 to 4%; or from 4 to 5%; or from 5 to 10%; or from 10 to 15%; or from 15 to 20%; or from 20 to 25%; or from 25 to 30%; or from 30 to 35%; or from 35 to 40%; or from 40 to 45%; or from 45 to 50%; or from 50 to 55%; or from 55 to 60%; or from 60 to 65%; or from 65 to 70%; or from 70 to 75%; or from 75 to 80%; or from 80 to 85%; or from 85 to 90%; or from 90 to 95%; from 95 to 99.9% of the total dry weight of the starting material.

When the starting material comprises CBD, the CBD can represent from 0.01 to 9.9%, and preferably from 0.1 to 95% of the total dry weight of the starting material. For example, CBD can represent from 0.01 to 0.1%; or from 0.1 to 0.5%; or from 0.5 to 1%; or from 1 to 2%; or from 2 to 3%; or from 3 to 4%; or from 4 to 5%; or from 5 to 10%; or from 10 to 15%; or from 15 to 20%; or from 20 to 25%; or from 25 to 30%; or from 30 to 35%; or from 35 to 40%; or from 40 to 45%; or from 45 to 50%; or from 50 to 55%; or from 55 to 60%; or from 60 to 65%; or from 65 to 70%; or from 70 to 75%; or from 75 to 80%; or from 80 to 85%; or from 85 to 90%; or from 90 to 95%; from 95 to 99.9% of the total dry weight of the starting material.

The starting material comprises one or more additional compounds and optionally further compounds, to be separated from the at least one cannabinoid compound.

In some variations, the additional compounds and/or further compounds may comprise or consist of cannabinoid compounds, which may in particular selected from the above list.

For example, the compound to be purified may be CBD, and the additional compounds and/or further compounds, to be separated from it, may comprise or consist of $\Delta^9$-THC and/or CBN. Or the compound to be purified may be CBN, and the additional compounds and/or further compounds, to be separated from it, may comprise or consist of $\Delta^9$-THC and/or CBD. Or the compound to be purified may be $\Delta^9$-THC, and the additional compounds and/or further compounds, to be separated from it, may comprise or consist of CBD and/or CBN.

In some variations, the additional compounds and/or further compounds may comprise or consist of pesticides and/or plant growth regulators.

Pesticides are substances intended to repel, kill or control any species designated as "pest", including weed, insects, rodents, fungi or other organisms. Pesticides include herbicides, insecticides, rodenticides, fungicides and bactericides.

Plant growth regulators are substances or mixture of substances intended for accelerating or retarding the rate of growth or rate of maturation, or for otherwise altering the behavior of plants or the produce thereof. Plant nutrients, trace elements, nutritional chemicals, plant inoculants and soil amendments are not considered as plant growth regulators.

Examples of pesticides and plant growth regulators include daminozide, neonicotinoids such as e.g. imidacloprid and thiamethoxam, strobilurins such as e.g. azoxystrobin and trifloxystrobin, triazoles such as myclobutanil, avermectin, etoxazole, bifenazate as well as their derivatives.

According to some embodiments, the starting material comprises one single additional compound which is to be separated from the at least one cannabinoid compound.

According to other embodiments, the starting material comprises several additional compounds and/or further compounds which are to be separated from the at least one cannabinoid compound.

In some embodiments, the additional compounds and/or further compounds comprise or consist of one or more cannabinoid compounds on the one hand, plus one or more pesticides and/or plant growth regulators on the other hand.

According to some embodiments, the starting material may comprise from 0.01 to 50% of the one or more additional compounds and/or further compounds, and preferably from 0.1 to 50% of the one or more additional compounds and/or further compounds, based on the total dry weight of the starting material. For example, the starting material may comprise from 0.01 to 0.1%; or from 0.1 to 0.5%; or from 0.5 to 1%; or from 1 to 2%; or from 2 to 3%; or from 3 to 4%; or from 4 to 5%; or from 5 to 10%; or from 10 to 15%; or from 15 to 20%; or from 20 to 25%; or from 25 to 30%; or from 30 to 35%; or from 35 to 40%; or from 40 to 45%; or from 45 to 50% of the one or more additional compounds and/or further compounds.

In particular, the starting material may comprise from 0.01 to 50% of one or more plant growth regulators and/or pesticides, and preferably from 0.1 to 50% of one or more plant growth regulators and/or pesticides, based on the total dry weight of the starting material. For example, the starting material may comprise from 0.01 to 0.1%; or from 0.1 to 0.5%; or from 0.5 to 1%; or from 1 to 2%; or from 2 to 3%; or from 3 to 4%; or from 4 to 5%; or from 5 to 10%; or from 10 to 15%; or from 15 to 20%; or from 20 to 25%; or from 25 to 30%; or from 30 to 35%; or from 35 to 40%; or from 40 to 45%; or from 45 to 50% of one or more plant growth regulators and/or pesticides. One advantage of the present invention is that it makes it possible to separate cannabinoid compounds from chemicals such as plant growth regulators and/or pesticides which may be present in minute amounts in a starting material.

Apart from the at least one cannabinoid compound to be purified and the one or more additional compounds and/or further compounds, the starting material may also comprise natural waxes, terpenes and flavonoids.

The starting material may be an extract obtained from a *Cannabis* plant. The *Cannabis* plant may include different species including hemp and marijuana. The starting material can be a *Cannabis* extract, notably a hemp extract, or a marijuana extract, or a mixture derived from one of those. By "marijuana extract" is meant an extract wherein $\Delta^9$-THC is the major cannabinoid compound. By "hemp extract" is meant an extract enriched in CBD, and/or wherein CBD is the major cannabinoid compound and wherein $\Delta^9$-THC is found in low levels.

The starting material may be obtained by extracting *Cannabis* flos with a non-polar solvent, an alcohol (such as ethanol) or liquid carbon dioxide, preferably with a non-polar solvent. Any non-polar solvent capable of solubilizing the *Cannabis* plant can be used. Preferred non-polar solvent include liquid non-polar solvents comprising C5 to C12, preferably C5 to C8 straight chain or branched chain alkanes. More preferably the non-polar solvent is hexane or heptane.

The starting material may be prepared by solubilizing a part of the *Cannabis* plant in an extraction solvent, removing insoluble material from the resulting solution and removing the extraction solvent from the solution to form the initial mixture containing the at least one cannabinoid compound.

Main Stationary Phase

In the main purification stage, use is made of a main stationary phase, which comprises silica particles or preferably consists of silica particles.

These silica particles invention form a so-called silica gel when in solution. They comprise amino and/or diol groups on their surface. In other words, the silica particles comprise grafted functions of amines and/or diols. When used in a chromatographic installation, the silica particles form a normal phase, which means that the silica particles are mostly polar and separation between species is believed to mostly rely on polar interactions between the various species and the particles.

The silica particles may in particular comprise groups of formula (I) on their surface: (I) —Si—R—NH$_2$, wherein R is a linker group which may for instance comprise from 1 to 20 carbon atoms, preferably from 1 to 10 carbon atoms, more preferably from 1 to 4 carbon atoms, and optionally at least one heteroatom, preferably oxygen. R may in particular be (CH$_2$—CH$_2$) or (CH$_2$—CH$_2$—CH$_2$). Alternatively, the silica particles may comprise groups of formula (II) on their surface: (II) —Si—R$_1$(OH)—R$_2$(OH), wherein R$_1$ and R$_2$ are linker groups, each of which may for instance comprise from 1 to 20 carbon atoms, preferably from 1 to 10 carbon atoms, more preferably from 1 to 6 carbon atoms, and optionally at least one heteroatom, preferably oxygen. R$_1$ may in particular be (CH$_2$)$_m$—O—(CH$_2$)$_n$, wherein m and n are integers preferably from 1 to 4, more preferably from 1 to 3, and for instance m=3 and n=1. R$_2$ may in particular be (CH$_2$)$_m$ wherein m is an integer preferably from 1 to 3, or from 1 to 2, and most preferably m is 1.

The silica particles may preferably have an average volume diameter (Dv50) equal to or less than 200 μm, or 150 μm, or 100 μm, or 50 μm, or 20 μm.

In some embodiments, the Dv50 of the silica particles is from 1 μm to 50 μm, preferably from 2 μm to 30 μm, or from 5 μm to 20 μm.

The term Dv50 refers to the 50th percentile of the particle size distribution, i.e. 50% of the particles have a size (corresponding to the diameter of the particles, when the particles are spherical) less than the Dv50 and 50% have a size larger than the Dv50. This is the median of the volumetric distribution of silica particles.

Preferably, the distribution of the volume diameter of the particles of silica has only one peak (monodispersed distribution). The uniformity coefficient of this distribution may for example be less than or equal to 1.5, or less than or equal to 1.3, or less than or equal to 1.15. The particle size distribution of the silica particles may be determined by laser granulometry (NF 13320 standard).

Main Purification Stage

In the main purification stage, the at least one cannabinoid compound is substantially separated from the one or more additional compounds in a chromatographic installation.

As a first step, the initial mixture is put into contact with the main stationary phase comprising silica particles as described above, by injecting the initial mixture onto said main stationary phase.

Before the initial mixture is put into contact with the main stationary phase, it may optionally be diluted or dissolved (if it is a dry extract) in a solvent, or alternatively be used as such. Solvents which can be used for dissolving the initial mixture include C5-C12 alkanes such as heptane and hexane, alcohols such as ethanol, or their mixtures. These solvents are preferably similar to the elution solution described below but not limited to it.

Then, an elution step is performed by passing an elution solution through the main stationary phase. Optionally, this is followed by a washing step which is performed by passing a washing solution through the main stationary phase.

At least one fraction is collected at the elution step.

If the washing step is carried out, at least one fraction is collected at the washing step.

In some embodiments, a single fraction is collected at the elution step. In other embodiments, at least two fractions are collected at the elution step.

In some embodiments, a single fraction is collected at the washing step. In other embodiments, at least two fractions are collected at the washing step.

More than one fraction may be collected at different points in time in a given step.

At least one of the collected fractions contains the at least one (desired) cannabinoid compound purified from the one or more additional compounds, which means that the fraction in enriched in the at least one cannabinoid compound and depleted in the one or more additional compounds.

By a fraction "enriched" in one species A and "depleted" in one species B, it is meant that the ratio of species A/species B weight concentrations in the fraction is greater than that of the initial mixture (independently of the effects of concentration or overall dilution).

The ratio may be greater by at least a factor of 10 or 100 or 1000 or 10000.

The weight proportion of the purified at least one cannabinoid compound relative to the amount of the at least one cannabinoid compound present in the initial mixture may be at least 95%, preferably at least 98%, more preferably at least 99%, and most preferably at least 99.5% or 99.9%.

The weight proportion of the one or more additional compounds recovered in the at least one elution fraction or washing fraction comprising the purified at least one cannabinoid compound relative to the amount present in the initial mixture may be less than 5%, preferably at least 2%, more preferably less than 1%, and most preferably less than 0.5% or less than 0.1%.

The weight proportion of the one or more additional compounds relative to the purified at least one cannabinoid compound, in the at least one elution fraction or washing fraction comprising the purified at least one cannabinoid compound, may in particular be less than 2%, preferably less than 1%, more preferably less than 0.5%, most preferably less than 0.1% or less than 0.05% or less than 0.01%.

Other collected fractions may be enriched in one or several of the one or more additional compounds and depleted in the at least one (desired) cannabinoid compound.

The weight proportion of the one or more additional compounds recovered in fractions other than the fraction containing the purified at least one cannabinoid compound, relative to the amount present in the initial mixture, may be at least 95%, preferably at least 98%, more preferably at least 99%, and most preferably at least 99.5% or 99.9%.

In some embodiments, the fraction containing the purified at least one cannabinoid compound is obtained at the elution step.

In some embodiments, at least one fraction enriched in additional compound(s) may be obtained at the elution step.

In some embodiments, at least one fraction enriched in additional compound(s) may be obtained at the washing step.

In some embodiments, at least one fraction enriched in additional compound(s) may be obtained at the elution step and at least one fraction enriched in other additional compound(s) may be obtained at the washing step.

In some embodiments, at least part, and possibly all of the additional compounds present in the initial mixture have a stronger affinity for the main stationary phase than the at least one cannabinoid compound and are therefore retained on it, during the elution step (and optionally washed during the washing step).

In some embodiments, at least part, and possibly all of the additional compounds have a weaker affinity for the main stationary phase than the at least one cannabinoid compound and are therefore eluted during the elution step before the at least one cannabinoid compound, and collected separately.

In some embodiments, some of the additional compounds have a weaker affinity for the main stationary phase than the at least one cannabinoid compound and others of the additional compounds have a stronger affinity for the main stationary phase than the at least one cannabinoid compound. These respective additional compounds are thus collected in different fractions.

In some exemplary embodiments, during the elution step, one first fraction containing a mixture of cannabinoid compounds (including for example $\Delta^9$-THC, CBD and CBN) is recovered, as well as one or more other fractions containing additional compounds (such as pesticides or plant growth regulators) which may for instance be more polar than the cannabinoid compounds. The first fraction is substantially free from these additional compounds. Neonicotinoids (such as thiamethoxam and imidacloprid) are examples of such additional compounds. Other additional compounds may be coeluted in the first fraction, and may be separated at another stage. Yet other additional compounds may remain bound to the main stationary phase and may be released and collected in a fraction during a subsequent washing step.

In other exemplary embodiments, during the elution step, two or more fractions containing cannabinoid compounds may be recovered, and optionally at least another fraction containing additional compounds (such as pesticides or plant growth regulators), which may for instance be non-polar, may be separately recovered. Strobilurins, such as trifloxystrobin are examples of such additional compounds. The fractions containing cannabinoid compounds may be for instance one fraction containing $\Delta^9$-THC on the one hand and another fraction containing CBD and CBN on the other hand; or one fraction containing $\Delta^9$-THC, one fraction containing CBD, and one fraction containing CBN. Each of the above fractions may be substantially free from the compounds indicated as being contained in another fraction. Further additional compounds may remain bound to the main stationary phase and may be released and collected in a fraction during a subsequent washing step.

In other exemplary embodiments, some or all of the additional compounds are eluted during the elution step, while the at least one cannabinoid compound remains bound to the main stationary phase. The at least one cannabinoid compound can then be collected during a subsequent washing step, as a fraction substantially free from the additional compounds eluted during the elution step.

The elution solution may be a non-polar solvent. The elution solution can also, more preferably, be a mixture of a polar and a non-polar solvent.

By "polar solvent" is herein meant a solvent having a dielectric constant at a temperature of 20° C. which is at least 15. By "non polar solvent" is herein meant a solvent having a dielectric constant at a temperature of 20° C. which is less than 15.

The polar solvent can in particular be an alcohol, such as ethanol or methanol, water and mixtures thereof. Preferably, ethanol is used as a polar solvent.

The non-polar solvent can in particular be an alkane, preferably a C5 to C10 alkane. More preferably, the non-polar solvent can be selected from pentane, hexane, heptane and octane. According to preferred embodiments, the non-polar solvent is hexane or heptane, more preferably heptane.

The elution may be performed in isocratic mode or gradient mode. In the isocratic mode, the composition of the elution solution remains constant during the elution step. In the gradient mode, the composition of the elution solution varies during the elution step. In particular, the volume proportion of polar solvent to non-polar solvent in the elution solution may vary during the elution step. In particular, the volume proportion of polar solvent to non-polar solvent in the elution solution may increase during the elution step. The isocratic mode is however preferred.

The elution solution can have a volume ratio of non-polar solvent to polar solvent from 99/1 to 50/50. More preferably, this volume ratio is from 98/2 to 60/40. Therefore, the volume ratio of non-polar solvent to polar solvent of the elution solution can be for instance from 99/1 to 90/10; or from 90/10 to 80/20; or from 80/20 to 70/30; or from 70/30 to 60/40; or from 60/40 to 50/50.

In the optional washing step, the main stationary phase can be washed with a washing solution. During this step, compounds retained on the main stationary phase can be washed and optionally recovered, as one or more fractions.

The washing solution may be a polar solvent. The washing solution can also, more preferably, be a mixture of a polar and a non-polar solvent.

The polar solvent can in particular be an alcohol such as ethanol or methanol, water and mixtures thereof. Preferably, ethanol is used as a polar solvent.

The non-polar solvent in particular be an alkane, preferably a C5 to C10 alkane. More preferably, the non-polar solvent can be selected from pentane, hexane, heptane and octane. According to preferred embodiments, the non-polar solvent is hexane or heptane, heptane being more preferred.

The washing solution can notably have a volume ratio of non-polar solvent to polar solvent from 1/99 to 50/50. More preferably, this volume ratio is from 2/98 to 40/60. Therefore, the volume ratio of non-polar solvent to polar solvent of the washing solution can be from 1/99 to 10/90; or from 10/90 to 20/80; or from 20/80 to 30/70; or from 30/70 to 40/60; or from 40/60 to 50/50.

Preferably, the washing solution is more polar (i.e. contains a larger relative proportion of polar solvent) than the elution solution.

The washing may be performed in isocratic mode or gradient mode. In the isocratic mode, the composition of the washing solution remains constant during the washing step. In the gradient mode, the composition of the washing solution varies during the washing step. In particular, the volume proportion of polar solvent to non-polar solvent in the washing solution may vary during the washing step. In particular, the volume proportion of polar solvent to non-polar solvent in the washing solution may increase during the washing step. The isocratic mode is however preferred.

Optionally, the main stationary phase can be equilibrated by putting it in contact with an equilibration solution. This step makes the adsorption sites of the main stationary phase available for another purification.

The equilibration solution may be a non-polar solvent. The equilibration solution can also, more preferably, be a mixture of a polar and a non-polar solvent.

The polar solvent can in particular be an alcohol such as ethanol or methanol, water and mixtures thereof. Preferably, ethanol is used as a polar solvent.

The non-polar solvent can in particular be an alkane, preferably a C5 to C10 alkane. More preferably, the non-polar solvent can be selected from pentane, hexane, heptane and octane. According to preferred embodiments, the non-polar solvent is hexane or heptane, heptane being more preferred.

The equilibration solution can notably have a volume ratio of non-polar solvent to polar solvent from 99/1 to 50/50. More preferably, this volume ratio is from 98/2 to 60/40. Therefore, the volume ratio of non-polar solvent to polar solvent of the equilibration solution can be from 99/1 to 90/10; or from 90/10 to 80/20; or from 80/20 to 70/30; or from 70/30 to 60/40; or from 60/40 to 50/50.

Preferably, the equilibration solution is the same as the elution solution.

Preliminary Purification Stage by Chromatographic Purification

The method of the invention may comprise two successive stages, a preliminary purification stage or pretreatment (described below) and a main purification stage (described above). In the preliminary stage, the initial mixture is prepared from a preliminary mixture corresponding to the starting material described above. In this stage, use is made of a preliminary stationary phase.

The preliminary purification stage may be a stage of chromatographic purification.

The preliminary stationary phase may be the same or different from the main stationary phase.

According to some embodiments, the preliminary stationary phase may comprise silica particles. In particular, the preliminary stationary phrase may comprise or consist of silica particles comprising amino and/or diol groups, as described above.

If the preliminary and main stationary phases are the same, use may be made of two different beds of the same stationary phase, for instance in two different chromatographic installations. Alternatively, the preliminary and main stationary phases may be the same bed in the same chromatographic installation, successively used at different points in time.

According to some embodiments, the preliminary stationary phase may comprise or consist of non-functionalized silica particles.

During a first step, the preliminary mixture is put in contact with the preliminary stationary phase by injecting the preliminary mixture onto the preliminary stationary phase.

An elution is then carried out with an elution solution in order to collect one or more preliminary elution fractions, optionally followed by a washing step with a washing solution in order to collect one or more preliminary washing fractions.

At least one preliminary elution fraction is collected at the elution step.

If the washing step is carried out, at least one preliminary washing fraction is collected at the washing step.

In some embodiments, a single preliminary elution fraction is collected at the elution step. In other embodiments, at least two preliminary elution fractions are collected at the elution step.

In some embodiments, a single preliminary washing fraction is collected at the washing step. In other embodiments, at least two preliminary washing fractions are collected at the washing step.

More than one preliminary fraction may be collected at different points in time in a given step.

At least one of the preliminary elution fractions or the preliminary washing fractions is a liquid fraction enriched in the at least one cannabinoid compound and the one or more additional compounds and depleted in the further compounds. Said liquid fraction provides the initial mixture and is used in the main purification stage.

Each elution step, each elution solution, each washing step and each washing solution may be as described in more detail above with respect to the main purification stage. The elution solution of the preliminary purification stage may be the same as the elution solution of the main purification stage, or preferably different.

In some embodiments, the elution solution of the main purification stage is more polar than the elution solution of the preliminary purification stage.

In some embodiments, the elution solution of the main purification stage is less polar than the elution solution of the preliminary purification stage.

The elution solution of the preliminary purification stage is preferably a mixture of a polar and a non-polar solvent.

The polar solvent can in particular be an alcohol, such as ethanol or methanol, water and mixtures thereof. Preferably, ethanol is used as a polar solvent.

The non-polar solvent can in particular be an alkane, preferably a C5 to C10 alkane. More preferably, the non-polar solvent can be selected from pentane, hexane, heptane and octane. According to preferred embodiments, the non-polar solvent is hexane or heptane, more preferably heptane.

The elution solution of the preliminary purification stage can have a volume ratio of non-polar solvent to polar solvent from 99/1 to 50/50. More preferably, this volume ratio is from 98/2 to 60/40. Therefore, the volume ratio of non-polar solvent to polar solvent of the elution solution of the preliminary purification stage can be for instance from 99/1 to 90/10; or from 90/10 to 80/20; or from 80/20 to 70/30; or from 70/30 to 60/40; or from 60/40 to 50/50.

The preliminary stationary phase may be equilibrated after the elution and optional washing of the preliminary purification stage, as described above with respect to the main purification stage. This is useful in particular if it is to be used again as the main stationary phase at the main purification stage.

This variant may be advantageous in order to separate the at least one cannabinoid compound from several different compounds or groups of compounds. At the preliminary purification stage, the at least one cannabinoid compound is separated from the further compounds but is substantially not separated from the additional compounds.

As a result, the initial mixture provided by the preliminary purification stage is enriched in the at least one cannabinoid compound and the additional compounds and depleted in the further compounds, relative to the preliminary mixture.

The ratio of the weight concentration of the at least one cannabinoid compound relative to the weight concentration of the further compounds is greater in the initial mixture than in the preliminary mixture, preferably by at least a factor of 10 or 100 or 1000 or 10000.

The weight proportion of the at least one cannabinoid compound in the initial mixture relative to the amount of the at least one cannabinoid compound present in the preliminary mixture may be at least 95%, preferably at least 98%, more preferably at least 99%, and most preferably at least 99.5% or 99.9%.

The weight proportion of the one or more further compounds recovered in the initial mixture relative to the amount present in the preliminary mixture may be less than 5%, preferably at least 2%, more preferably less than 1%, and most preferably less than 0.5% or less than 0.1%.

The weight proportion of the one or more further compounds relative to the at least one cannabinoid compound in the initial mixture may in particular be less than 2%, preferably less than 1%, more preferably less than 0.5%, most preferably less than 0.1% or less than 0.05% or less than 0.01%.

Then, at the main purification stage, the at least one cannabinoid compound is separated from the additional compounds. As a result, at the main purification stage, a fraction is collected which is enriched in the at least one cannabinoid compound and depleted in the additional compounds (relative to the initial mixture obtained after the preliminary purification stage).

The main benefits of a two-stage process are that the size of the columns and volumes of solvents can be adjusted to the specific separation of the at least one cannabinoid compound from the further compounds at the preliminary purification stage and to the specific separation of the at least one cannabinoid compound from the additional compounds at the main purification stage.

In preferred embodiments, the preliminary purification stage is designed to separate the at least one cannabinoid compound from strongly retained impurities (further compounds). The retention time differences being higher during the preliminary purification stage, a reduced amount of stationary phase and of solvents is required, compared to the main purification stage.

In some embodiments, the additional compounds may comprise non-polar plant growth regulators and/or pesticides (such as in particular strobilurins such as trifloxystrobin) and optionally cannabinoid compounds; and the further compounds may comprise polar plant growth regulators and/or pesticides (such as in particular neonicotinoids, e.g. imidacloprid and thiamethoxam and/or daminozide).

In the main purification stage, one particular (desired) cannabinoid compound, for instance selected from the group of CBN, CBD and $\Delta^9$-THC, may be separated from one or more other cannabinoid compounds, for instance also selected from the group of CBN, CBD and $\Delta^9$-THC, and may also be separated from non-polar plant growth regulators and/or pesticides (such as a strobilurin, e.g. trifloxystrobin). Several distinct fractions can thus be collected in the main purification stage.

Preliminary Purification Stage by Suspension Purification

As a variant to the above preliminary purification stage by chromatographic purification, the preliminary purification stage may also be conducted by putting the preliminary mixture in contact with the preliminary stationary phase, in a suspension solution to form a suspension. For example, the preliminary stationary phase may be mixed with the preliminary mixture (and the suspension solution), in a tank provided with stirring elements. Such stirring elements can for example include one or more agitators, a recirculation pump or the like. The tank may be for example a fluidized bed reactor. After a given residence time, the suspension can be filtered, collecting a first fraction on the one hand and the preliminary stationary phase on the other hand.

Optionally, the preliminary stationary phase may be resuspended in a further solution, and filtered so as to collect a further fraction. This step can be repeated several times if needed.

At least one of the first or the further fractions is a liquid fraction enriched in the at least one cannabinoid compound and the one or more additional compounds and depleted in the further compounds. Said liquid fraction provides the initial mixture and is used in the main purification stage.

The preliminary stationary phase used in the suspension purification may be the same as the preliminary stationary phase used in the preliminary chromatographic purification, as described above.

Alternatively, the preliminary stationary phase may comprise or consist of activated charcoal.

Alternatively, the preliminary stationary phase may comprise or consist of one or more zeolites.

The suspension solution may be an elution solution as described above in relation with the preliminary purification stage by chromatographic purification.

According to some embodiments, the further solution used for the resuspension of the preliminary stationary phase can also be an elution solution as described above in relation with the preliminary purification stage by chromatographic purification.

According to some embodiments, the further solution used for the resuspension of the preliminary stationary phase can be a washing solution as described above in relation with the preliminary purification stage by chromatographic purification.

According to some embodiments, and in case the preliminary stationary phase is resuspended more than once, for example two times, the first resuspension can be carried out with an elution solution as described above in relation with the preliminary purification stage by chromatographic purification, and the second resuspension can be carried out with a washing solution as described above in relation with the preliminary purification stage by chromatographic purification.

Optionally, the preliminary stationary phase can finally be suspended in an equilibration solution as described above in relation with the preliminary purification stage by chromatographic purification to achieve the equilibration of the preliminary stationary phase before reusing the preliminary stationary phase for another purification.

Chromatographic Installations and Operating Conditions

The method according to the invention may be discontinuous (or batch), semi-continuous or continuous.

The method according to the invention can be carried out at a constant temperature or at different successive temperatures. Preferably the temperature is substantially constant. The temperature at which the method is carried out may preferably range from 10 to 40° C., more preferably from 15 to 30° C. and most preferably from 20 to 25° C.

The term "chromatographic purification stages" used below, refers to the main purification stage as well as the preliminary purification stage when carried out by a chromatographic purification.

The chromatographic purification stages according to the invention are preferably carried out at a pressure from 1 to 100 bar and preferably from 10 to 40 bar.

The chromatographic purification stages according to the invention may be implemented in a chromatographic installation having a static bed or preferably in a chromatographic installation with a non-static bed.

In a chromatographic installation with a static bed, the mixture of compounds to be separated percolates in a generally cylindrical enclosure (or column). The column contains a bed of porous material (stationary phase) which is permeable to fluids. The percolation rate of each compound in the mixture depends on the physical properties of the compound. The most retained compounds on the stationary phase percolate more slowly than the less retained compounds on the stationary phase.

It is possible to carry out such a treatment in several columns in series or in parallel, but generally a chromatographic separation installation system with a static bed is applied with a single column.

Examples of such chromatographic installations with a static bed are the HPLC (High Performance Liquid Chromatography) or CYCLOJET™ (a system with recycling in the stationary state) systems.

The CYCLOJET™ system is as described in document U.S. Pat. No. 6,063,284, to which reference is expressly made. This is a discontinuous chromatographic separation installation with a single column, in which the most retained species (i) and then the less retained species (ii) are collected separately at the outlet of the column, the non-separated portion of the chromatogram being recycled by the main pump, and the mixture to be separated being periodically injected by means of an injection loop essentially located in the middle of the recycled portion of the chromatogram. After several chromatographic cycles, the process reaches a periodical stationary state in which the amount of injected products is equal to the amount of separated products collected separately at the outlet of the column.

An alternative of the CYCLOJET™ system using two columns is described in document U.S. Pat. No. 5,630,943, to which reference is expressly made.

An installation with a non-static bed is a multi-column installation, in which the relative positions of the stationary phase bed and of the injection or collecting points of the flows move over time.

Examples of such chromatographic installations with a non-static bed are the SMB (simulated moving bed), iSMB (improved simulated moving bed), SSMB (sequential simulated moving bed), AMB (actual moving bed), VARICOL™, MODICON™ POWERFEED™, MCSGP or GSSR (multi column gradient chromatography) systems.

An SMB system comprises a plurality of individual columns containing an adsorbent, which are connected in series. An eluent flow crosses the columns along a first direction. The injection points of the feed flow and of the eluent flow, as well as the points for collecting the separated compounds, are periodically and simultaneously shifted by means of a set of valves. The global effect is to simulate the operation of a single column containing a moving bed of solid adsorbent, the solid adsorbent moving in a counter current direction relatively to the eluent flow. Thus, an SMB system consists of columns which contain stationary beds of solid adsorbent through which the eluent passes, but the operation is such that a continuous moving bed as a counter current is simulated.

The most conventional form of an SMB system is the SMB system with four zones. Other possible forms are the SMB systems with three zones and the SMB systems with two zones (as described in the article "Two Section Simulated Moving Bed Process" of Kwangnam Lee, in Separation Science and Technology 35(4):519-534, 2000, to which reference is expressly made).

In the iSMB and SSMB systems, there is at least one step in which the system operates in a closed loop, without any product entry or exit.

An iSMB system is as described in documents EP 0 342 629 and U.S. Pat. No. 5,064,539, to which reference is expressly made.

An SSMB system divides the introductions and collections of the flows into subsequences applied periodically.

Other alternatives of the SMB systems are: the SMB system varying over time and the POWERFEED™ system, as described in document U.S. Pat. No. 5,102,553 and in the article "PowerFeed operation of simulated moving bed units: changing flow-rates during the switching interval", of Zhang et al. in Journal of Chromatography A, 1006:87-99, 2003, to which reference is expressly made; the MODICON™ system as described in document U.S. Pat. No. 7,479,228, to which is reference is expressly made; and the SMB system with internal recirculation, as described in document U.S. Pat. No. 8,282,831, to which reference is expressly made.

An AMB system has an operation similar to an SMB system. However, instead of displacing the feed flow and eluent injection points, as well as the collecting points, by means of a set of valves, a set of adsorption units (columns) are physically displaced relatively to the feed and collecting points. Again, the operation allows simulation of a continuous counter current moving bed.

A VARICOL™ chromatography system is as described in documents U.S. Pat. Nos. 6,136,198, 6,375,839 6,413,419 and 6,712,973, to which reference is expressly made. A VARICOL™ system comprises a plurality of individual columns containing an adsorbent, which are connected in series. An eluent is passed into the columns along a first direction. The injection points for the mixture to be separated and for the eluent and the points for collecting the separated compounds in the system are periodically displaced asynchronously, by means of a set of valves. The global effect is to generate separation zones with a variable length over time, thereby allocating the stationary phase dynamically in the zones where it is the most useful, and allowing a similar power of separation with less chromatographic separation units and increased productivity.

The chromatographic purification stages of the present invention may be carried out in a single-column chromatographic installation.

The chromatographic purification stages of the present invention may also be carried out in a multicolumn chromatographic installation with a discontinuous feed injection, such as but not limited to BioSC (as described in document EP 2040811) or DCC processing (as described in document EP 1912716).

The chromatographic purification stages of the present invention are preferably carried out in a high-pressure liquid chromatography installation.

According to some embodiments, the method of the invention only comprises the main purification stage (without the preliminary purification stage) and it can be performed in a single column installation, or in a two or three-column installation chosen between MCSGP or GSSR or DCC, or in a four or five or six or seven or eight-column installation chosen between SMB, iSMB, SSMB, AMB, VARICOL™, MODICON™ and POWERFEED™ In all of the above installations, the total bed length for the stationary phase preferably ranges from 10 cm to 100 cm.

According to some embodiments, the method of the present invention comprises the preliminary purification stage and the main purification stage and:

The preliminary purification stage may be carried out by using a single column installation, or by using a two or three-column installation such as DCC, or by using a four or five or six or seven or eight-column installation chosen between BioSC, SMB, iSMB, SSMB, AMB, VARICOL™, MODICON™ and POWERFEED™. In all of the above installations, the total bed length for the stationary phase preferably ranges from 10 cm to 100 cm.

The main purification stage may be carried out by using a single column installation, or by using a two or three-column installation chosen between MCSGP or GSSR or DCC, or by using a four or five or six or seven or eight-column installation chosen between SMB, iSMB, SSMB, AMB, VARICOL™, MODICON™ and POWERFEED™ In all of the above installations, the total bed length for the stationary phase preferably ranges from 10 cm to 100 cm.

The chromatographic purification stages of the present invention may be carried out in one or more installations comprising one or more chromatographic columns having a diameter (internal diameter) equal to or larger than 5 cm. For example, the diameter of the one or more chromatographic columns can be from 5 to 10 cm; or from 10 to 20 cm; or from 20 to 30 cm; or from 30 to 40 cm; or from 40 to 50 cm; or from 50 to 100 cm; or from 100 to 150 cm; or from 150 to 200 cm.

The chromatographic installation(s) used in the present invention may have a total dead volume lower than or equal to 30%, preferably lower than or equal to 20%, more preferably lower than or equal to 10% and even more preferably lower than or equal to 5% of the total volume of (main and/or preliminary) stationary phase in the installation (i.e. the volume of the bed of stationary phase).

The term "dead volume" can be defined as the sum of:
the volumes of piping in the chromatographic installation between a valve of the inlet for the injection of the feed (initial mixture or preliminary mixture) and the inlet of the bed of the stationary phase;
the volumes of piping in the chromatographic installation between an outlet of the bed of the stationary phase and a valve of the outlet for the collection of the product of interest;
the volumes of piping in the chromatographic installation connecting any column in series between a valve of the outlet for the collection of the product of interest and a valve of the inlet for the injection of the feed (initial mixture or preliminary mixture), if the installation is multicolumn.

The velocity of the fluids at the entrance of the bed of (main and/or preliminary) stationary phase can be from 30 cm/hour to 5000 cm/hour, preferably from 100 to 4000 cm/hour, and more preferably from 200 to 3000 cm/hour. For example, this velocity can be from 30 to 40 cm/hour; or from 40 to 50 cm/hour; or from 50 to 60 cm/hour; or from 60 to 70 cm/hour; or from 70 to 80 cm/hour; or from 80 to 90 cm/hour; or from 90 to 100 cm/hour; or from 100 to 250 cm/hour; or from 250 to 500 cm/hour; or from 500 to 750 cm/hour; or from 750 to 1000 cm/hour; or from 1000 to 1500 cm/hour; or from 1500 to 2000 cm/hour; or from 2000 to 3000 cm/hour; or from 3000 to 4000 cm/hour; or from 4000 to 5000 cm/hour.

These ranges may apply to the initial mixture, and/or the preliminary mixture, and/or the elution solution, and/or the washing solution, and/or the equilibration solution.

The velocity of the liquid can be constant over the various steps of one chromatographic stage (either the main purification stage or the preliminary purification stage carried out by chromatographic purification).

Alternatively, the velocity of the liquid can vary during one chromatographic stage. For example, the velocity of the initial mixture or the preliminary mixture can be lower than the velocity of the elution solution, and/or the velocity of the initial mixture or the preliminary mixture can be lower than the velocity of the washing solution, and/or the velocity of the initial mixture or the preliminary mixture can be lower than the velocity of the equilibration solution. Otherwise, the velocity of the initial mixture or the preliminary mixture can be higher than the velocity of the elution solution, and/or the velocity of the initial mixture or the preliminary mixture can be higher than the velocity of the washing solution, and/or the velocity of the initial mixture or the preliminary mixture can be higher than the velocity of the equilibration solution.

Similarly, the velocity of the elution solution, the washing solution and the equilibration solution may be different, lower or higher from one another.

EXAMPLES

The following examples illustrate the invention without limiting it.

The starting material to be purified comprises $\Delta^9$-tetrahydrocannabinol, cannabidiol, cannabinol, daminozide, imidacloprid, thiamethoxam and trifloxystrobin.

Example 1—Chromatographic Separation of Imidacloprid and Thiamethoxam

In this example, the invention is applied on a HPLC Agilent 1100.

The stationary phase used is Amino 10 µm, M.S. Gel and a mixture of ethanol and heptane in a volume ratio of 60/40 heptane/ethanol is used as the mobile phase.

As shown in FIG. 1, the cannabinoid compounds $\Delta^9$-THC, CBD and CBN (A) co-elute with trifloxystrobin (B), while imidacloprid (C) and thiamethoxam (D) are successfully separated. Furthermore, daminozide (not shown in FIG. 1) remains retained in the stationary phase.

Example 2—Chromatographic Separation of Daminozide, Imidacloprid and Thiamethoxam This example is similar to example 1, expect that the stationary phase used is Daisogel Diol 10 µm. A mixture of ethanol and heptane in a volume ratio of 60/40 heptane/ethanol is still used as the mobile phase.

Figure 2:
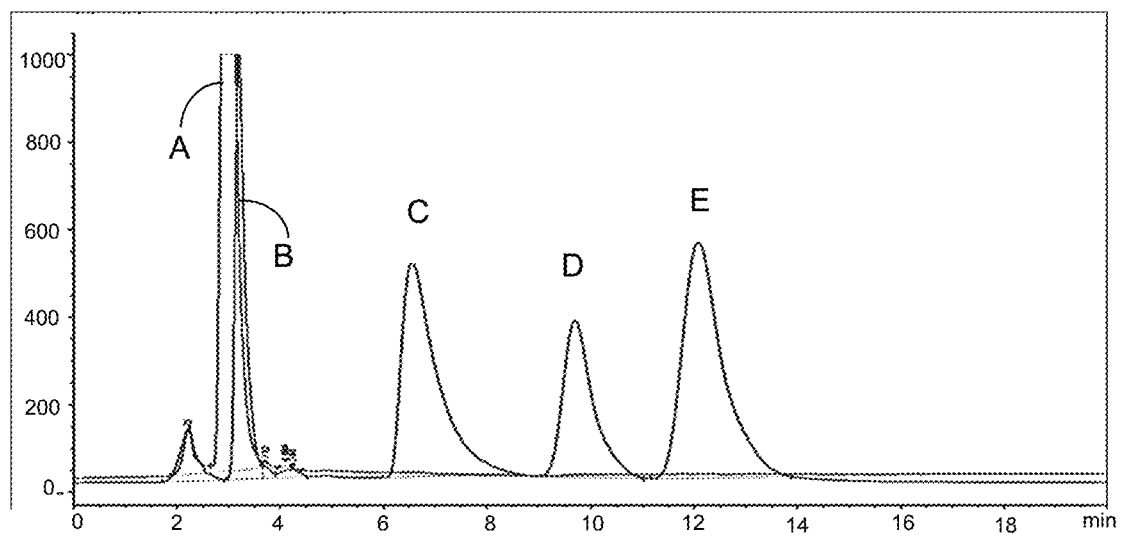

As shown in FIG. 2, the cannabinoid compounds $\Delta^9$-THC, CBD, and CBN (A) co-elute with trifloxystrobin (B), while daminozide (C), imidacloprid (D) and thiamethoxam (E) are successfully separated.

Example 3—Chromatographic Separation of Trifloxystrobin and $\Delta^9$-THC

This example is similar to example 1, expect that a less polar mixture of ethanol and heptane in a volume ratio of 98/2 heptane/ethanol is used as the mobile phase.

Figure 3:
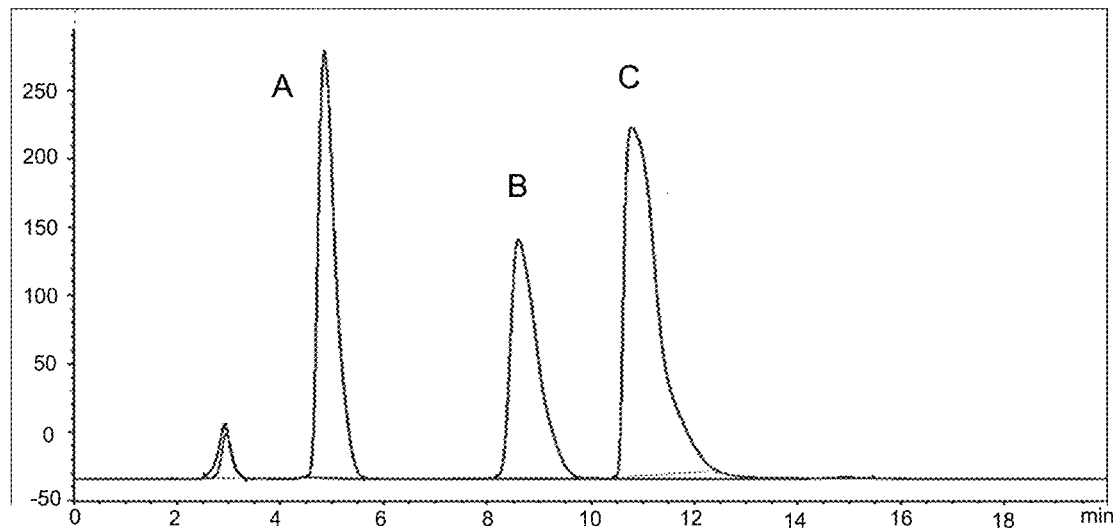

As shown in FIG. 3, trifloxystrobin (A) and $\Delta^9$-THC (B) no longer co-elute, while CBD, and CBN (C) still elute together. Furthermore, daminozide, imidacloprid, and thiamethoxam (not shown in FIG. 3) remain retained on the stationary phase.

Example 4—Chromatographic Separation of Trifloxystrobin, $\Delta^9$-THC, CBN and CBD This example is similar to example 2, expect that a mixture of ethanol and heptane in a volume ratio of 98/2 heptane/ethanol is used as the mobile phase.

Figure 4:
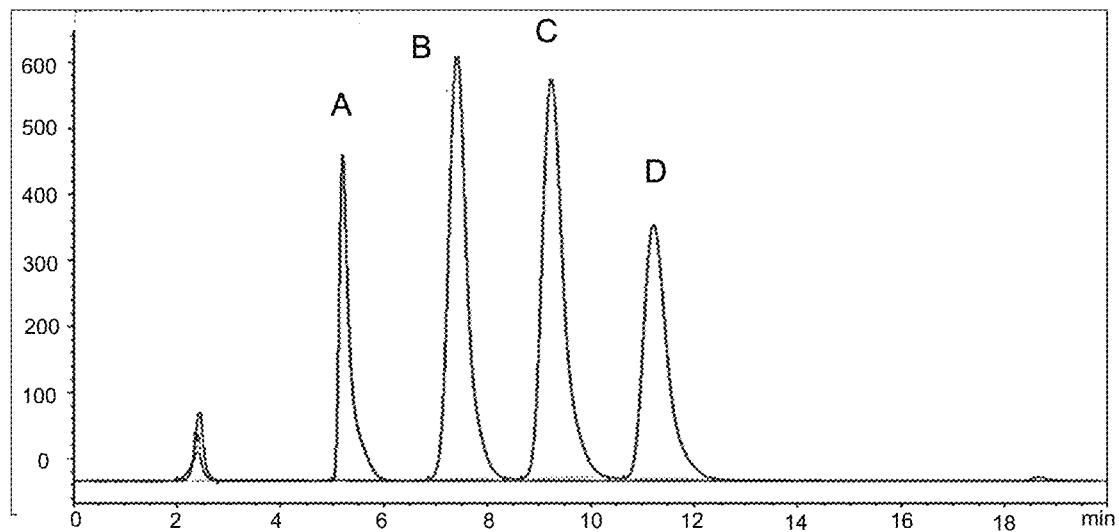

As shown in FIG. 4, trifloxystrobin, (A), $\Delta^9$-THC (B), CBN (C) and CBD (D) are successfully separated. Daminozide, imidacloprid, and thiamethoxam (not shown in FIG. 3) remain retained on the stationary phase.

Example 5—Chromatographic Separation of Trifloxystrobin, $\Delta^9$-THC, CBN, CBD, Daminozide, Imidacloprid and Thiamethoxam In this example, the invention is implemented on a High-Pressure Liquid Chromatography installation.

The stationary phase used is Daisogel Diol 10 µm.

Figure 5:
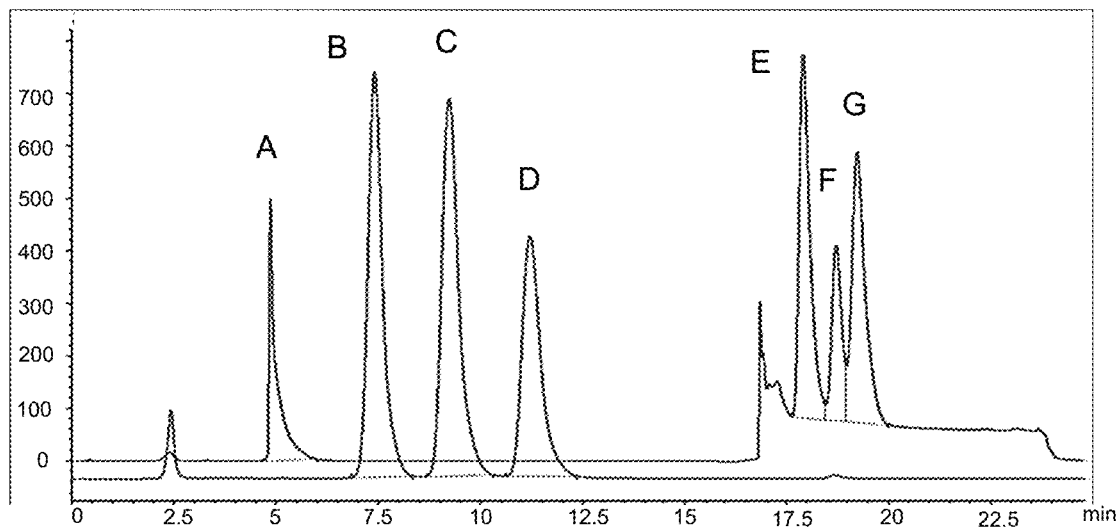

Firstly, the stationary phase is eluted with a mixture of ethanol and heptane in a volume ratio of 98/2 heptane/ethanol and as shown in FIG. 5. Within the first 13 minutes, trifloxystrobin (A), $\Delta^9$-tetrahydrocannabinol (B), cannabinol (C), and cannabidiol (D) are purified.

Then washing is performed with a more polar mixture of ethanol and heptane (volume ratio of 20/80 heptane/ethanol) in order to collect the more polar daminozide (E), imidacloprid (F), and thiamethoxam (G).

Finally, a mixture of ethanol and heptane in a volume ratio of 98/2 heptane/ethanol is used for the equilibration of the stationary phase.

Example 6—Two Step Chromatographic Separation of Trifloxystrobin, THC, CBN, CBD, Daminozide, Imidacloprid and Thiamethoxam In this example, the invention is applied on a HPLC Agilent 1100.

The stationary phase used is Daisogel Diol 10 µm.

In a first step, the stationary phase is eluted with a mixture of ethanol and heptane in a volume ratio of 60/40 heptane/ethanol and the so-called initial mixture is collected on the one hand, comprising $\Delta^9$-THC, CBN and CBD, while the more polar daminozide, imidacloprid, and thiamethoxam are successfully separated on the other hand.

In a second step, the initial mixture is loaded in a HPLC Agilent 1100 and the stationary phase is eluted with a mixture of ethanol and heptane in a volume ratio of 98/2 heptane/ethanol. At the end of this step, trifloxystrobin, $\Delta^9$-THC, CBN, and CBD are successfully purified.

These examples demonstrate that the separation of at least one cannabinoid compound from a starting material is possible and that the values of retention time can vary from one example to another or from one stationary phase to another. In fact, the difference in retention times which is observed is sufficient in order to purify the starting material at an industrial scale. From those examples, and using a chromatography simulation software, based for example on methods described in the *Preparative Chromatography of Fine Chemicals and Pharmaceutical Agents*, Henner Schmidt-Traub, Wiley-VCH, ISBN-13 978-3-527-30643-5, it is possible to produce a model from any chromatogram that presents a difference in retention times. This model makes it possible to predict that a purity higher than 99%, and a yield greater than 90% for the various tested cannabinoid compounds, can be achieved, for any initial weight proportions of cannabinoids and additional compounds in the starting material.

The invention claimed is:

1. A method for the chromatographic purification of at least one cannabinoid compound, wherein the method comprises a main purification stage comprising the steps of:
    injecting an initial mixture comprising the at least one cannabinoid compound and one or more additional compounds onto a main stationary phase comprising silica particles, the silica particles comprising amino and/or diol groups;
    performing an elution with an elution solution, and collecting at least two elution fractions, wherein the elution solution is a mixture comprising heptane and ethanol and wherein the elution is performed in an isocratic mode
    at least one of the elution fractions containing the at least one cannabinoid compound purified from the one or more additional compounds, and at least one other of the elution fractions containing at least one of the one or more additional compounds.

2. The method according to claim 1, which is carried out in an installation chosen from a single column installation, or a multi-column installation having a total bed length smaller than 100 cm.

3. The method of claim 1, wherein the one or more additional compounds comprise pesticides and/or growth regulators.

4. The method according to claim 1, wherein the volume ratio of heptane to ethanol in the elution solution is from 99/1 to 50/50.

5. The method according to claim 1, further comprising a preliminary purification stage before the main purification stage, said preliminary purification stage comprising the steps of:
putting a preliminary mixture comprising the at least one cannabinoid compound, the one or more additional compounds and one or more further compounds in contact with a preliminary stationary phase; and
collecting at least one liquid fraction enriched in the at least one cannabinoid compound and the one or more additional compounds and depleted in the further compounds, said at least one liquid fraction providing the initial mixture.

6. The method according to claim 5, wherein the one or more further compounds are selected from cannabinoid compounds, pesticides, plant growth regulators and combinations thereof.

7. The method according to claim 1, wherein the initial mixture is a *cannabis* extract and wherein the at least one cannabinoid compound is selected from $\Delta^9$-tetrahydrocannabinol, cannabidiol, cannabinol, cannabigerol, cannabichromene, cannabidivarol, tetrahydrocannabidiol, tetrahydrocannabidivarol, $\Delta^8$-tetrahydrocannabinol, carboxylic acid precursors of the foregoing compounds, and combinations thereof.

8. The method according to claim 1, wherein the weight proportion of the purified at least one cannabinoid compound relative to the amount of the at least one cannabinoid compound present in the initial mixture is at least 95%.

9. The method according to claim 1, wherein the at least one elution fraction containing the at least one cannabinoid compound purified from the one or more additional compounds further comprises a weight proportion of the one or more additional compounds which is less than 5%, relative to the amount of the one or more additional compounds present in the initial mixture.

10. A method for the chromatographic purification of at least one cannabinoid compound, wherein the method comprises a main purification stage comprising the steps of:
injecting an initial mixture comprising $\Delta^9$-tetrahydrocannabinol, cannabidiol and cannabinol onto a main stationary phase comprising silica particles, the silica particles comprising amino and/or diol groups; and
performing an elution with an elution solution wherein the elution solution is a mixture comprising heptane and ethanol, and collecting at least three elution fractions;
wherein at least one of the elution fractions contains $\Delta 9$-tetrahydrocannabinol, at least another of the elution fractions contains cannabidiol and at least yet another of the elution fractions contains cannabinol.

11. The method according to claim 10, wherein the volume ratio of heptane to ethanol in the elution solution is from 99/1 to 50/50.

12. The method according to claim 10, further comprising a preliminary purification stage before the main purification stage, said preliminary purification stage comprising the steps of:
putting a preliminary mixture comprising $\Delta^9$-tetrahydrocannabinol, cannabidiol and cannabinol and one or more further compounds in contact with a preliminary stationary phase; and
collecting at least one liquid fraction enriched in $\Delta^9$-tetrahydrocannabinol, cannabidiol and cannabinol and depleted in one or more of the further compounds, said at least one liquid fraction providing the initial mixture.

13. The method according to claim 12, wherein the one or more further compounds are selected from cannabinoid compounds, pesticides, plant growth regulators and combinations thereof.

14. A method for the chromatographic purification of at least one cannabinoid compound, wherein the method comprises a main purification stage comprising the steps of:
injecting an initial mixture comprising the at least one cannabinoid compound and one or more additional compounds onto a main stationary phase comprising silica particles, the silica particles comprising amino and/or diol groups;
performing an elution with an elution solution, and collecting one or more elution fractions, wherein the elution solution is a mixture comprising heptane and ethanol and wherein the elution is performed in an isocratic mode; and
washing the main stationary phase with a washing solution and collecting one or more washing fractions;
at least one of the elution fractions containing the at least one cannabinoid compound purified from the one or more additional compounds, and at least one of the washing fractions containing at least one of the one or more additional compounds.

15. The method of claim 14, wherein the one or more additional compounds comprise pesticides and/or growth regulators.

16. The method according to claim 14, wherein the volume ratio of heptane to ethanol in the elution solution is from 99/1 to 50/50.

17. The method according to claim 14, wherein the washing solution is a mixture of an alcohol and an alkane and has a volume ratio of alkane to alcohol from 1/99 to 50/50.

18. The method according to claim 14, wherein the initial mixture is a *cannabis* extract and wherein the at least one cannabinoid compound is selected from $\Delta^9$-tetrahydrocannabinol, cannabidiol, cannabinol, cannabigerol, cannabichromene, cannabidivarol, tetrahydrocannabidiol, tetrahydrocannabidivarol, $\Delta^8$-tetrahydrocannabinol, carboxylic acid precursors of the foregoing compounds, and combinations thereof.

19. The method according to claim 14, wherein the weight proportion of the purified at least one cannabinoid compound relative to the amount of the at least one cannabinoid compound present in the initial mixture is at least 95%.

20. The method according to claim 14, wherein the at least one elution fraction containing the at least one cannabinoid compound purified from the one or more additional compounds further comprises a weight proportion of the one or more additional compounds which is less than 5%, relative to the amount of the one or more additional compounds present in the initial mixture.

* * * * *